United States Patent
Goering et al.

(10) Patent No.: US 10,646,120 B2
(45) Date of Patent: May 12, 2020

(54) BODY-WORN BIOMETRIC SENSOR

(71) Applicant: Vytal Corporation, Wichita, KS (US)

(72) Inventors: Jared Goering, McPherson, KS (US); Spencer Steinert, McPherson, KS (US)

(73) Assignee: Vytal Corporation, Wichita, KS (US)

( * ) Notice: Subject to any disclaimer, the term of this patent is extended or adjusted under 35 U.S.C. 154(b) by 0 days.

(21) Appl. No.: 15/397,525

(22) Filed: Jan. 3, 2017

(65) Prior Publication Data
US 2018/0184914 A1 Jul. 5, 2018

(51) Int. Cl.
*A61B 5/0205* (2006.01)
*A41D 1/00* (2018.01)
(Continued)

(52) U.S. Cl.
CPC .......... *A61B 5/02055* (2013.01); *A41D 1/002* (2013.01); *A61B 5/0022* (2013.01); *A61B 5/01* (2013.01); *A61B 5/024* (2013.01); *A61B 5/0402* (2013.01); *A61B 5/04085* (2013.01); *A61B 5/1118* (2013.01); *A61B 5/14552* (2013.01); *A61B 5/6802* (2013.01); *A61B 5/6832* (2013.01); *A61B 2505/09* (2013.01); *A61B 2560/0214* (2013.01); *A61B 2562/0219* (2013.01)

(58) Field of Classification Search
None
See application file for complete search history.

(56) References Cited

U.S. PATENT DOCUMENTS

D379,936 S    6/1997   Wei-Hsin
6,605,046 B1 * 8/2003  Del Mar ............ A61B 5/04085
                                              600/507
(Continued)

FOREIGN PATENT DOCUMENTS

WO    WO2008006150    1/2008

OTHER PUBLICATIONS

"Smart Wellness Coaching," Retrieved from the internet on Jul. 3, 2018, Retrieved from the Internet: URL<https://www.firstbeat.com/en/>. 5 pages.
(Continued)

*Primary Examiner* — Carl H Layno
*Assistant Examiner* — Manolis Pahakis
(74) *Attorney, Agent, or Firm* — Fish & Richardson P.C.

(57) ABSTRACT

Systems and methods for tracking or viewing a user's physiological parameters before, during, and/or after physical activity. In some versions, a sensor device can be worn on a user's body and is configured to detect multiple physiological parameters and to wirelessly communicate with a mobile computing device. Optionally, the detected physiological parameters can be used to determine a selected set of work-out parameters, which can be concurrently displayed on the mobile computing device during the user's exercise/activity or after the exercise period. In some implementations, each of a plurality of users can wear a respective body-worn sensor device, and all of the sensors devices can wireless communicate with a designated mobile computing device for purposes of collectively (and concurrently) monitoring sets of physiological parameters for all of the users during the same workout, practice, or other activity.

23 Claims, 8 Drawing Sheets

(51) Int. Cl.
  *A61B 5/1455* (2006.01)
  *A61B 5/01* (2006.01)
  *A61B 5/11* (2006.01)
  *A61B 5/0408* (2006.01)
  *A61B 5/00* (2006.01)
  *A61B 5/0402* (2006.01)
  *A61B 5/024* (2006.01)

(56) References Cited

U.S. PATENT DOCUMENTS

| | | | |
|---|---|---|---|
| 7,257,438 B2 | 8/2007 | Kinast | |
| D615,657 S | 5/2010 | Anderson et al. | |
| D615,659 S | 5/2010 | Anderson et al. | |
| 7,970,450 B2 | 6/2011 | Kroecker et al. | |
| D658,768 S | 5/2012 | Parker et al. | |
| 8,180,425 B2* | 5/2012 | Selvitelli | A61B 5/04085 600/382 |
| 8,238,996 B2 | 8/2012 | Burnes et al. | |
| 8,613,709 B2* | 12/2013 | Bishay | A61B 5/02438 600/382 |
| D702,357 S | 4/2014 | Vosch et al. | |
| D704,575 S | 5/2014 | Maresova et al. | |
| D714,664 S | 10/2014 | Naughton et al. | |
| D736,107 S | 8/2015 | Lee | |
| D745,174 S | 12/2015 | Gaw | |
| D748,275 S | 1/2016 | Vosch et al. | |
| 9,226,679 B2* | 1/2016 | Balda | A61B 5/0006 |
| 9,237,848 B2* | 1/2016 | Russell | A61B 5/688 |
| D535,575 S | 3/2016 | Howansky et al. | |
| 9,277,864 B2* | 3/2016 | Yang | A61B 5/00 |
| 9,439,599 B2* | 9/2016 | Thompson | A61B 5/0006 |
| 9,597,004 B2* | 3/2017 | Hughes | A61B 5/6832 |
| D800,583 S | 10/2017 | Ahong et al. | |
| 9,848,779 B2* | 12/2017 | Lai | A61B 5/0002 |
| 2004/0073127 A1* | 4/2004 | Istvan | A61B 5/0006 600/513 |
| 2005/0280531 A1* | 12/2005 | Fadem | A61B 5/0006 340/539.12 |
| 2008/0108890 A1* | 5/2008 | Teng | A61B 5/04087 600/372 |
| 2008/0114220 A1* | 5/2008 | Banet | A61B 5/021 600/301 |
| 2008/0139953 A1* | 6/2008 | Baker | A61B 5/0006 600/509 |
| 2008/0309287 A1 | 12/2008 | Reed | |
| 2009/0036792 A1 | 2/2009 | DeLuca et al. | |
| 2010/0069735 A1* | 3/2010 | Berkner | A61B 5/04028 600/382 |
| 2010/0081913 A1* | 4/2010 | Cross | A61B 5/04085 600/386 |
| 2010/0317958 A1 | 12/2010 | Beck et al. | |
| 2010/0326703 A1 | 12/2010 | Gilad et al. | |
| 2011/0028822 A1 | 2/2011 | Beck | |
| 2011/0062241 A1 | 3/2011 | Beck | |
| 2012/0330126 A1* | 12/2012 | Hoppe | A61B 5/0002 600/391 |
| 2013/0116520 A1* | 5/2013 | Roham | A61B 5/6833 600/324 |
| 2013/0131484 A1* | 5/2013 | Pernu | A61B 5/0245 600/388 |
| 2014/0031663 A1* | 1/2014 | Gallego | A61B 5/04085 600/386 |
| 2014/0051946 A1* | 2/2014 | Arne | A61B 5/0022 600/301 |
| 2014/0189928 A1* | 7/2014 | Oleson | A61B 5/6823 2/69 |
| 2015/0087923 A1* | 3/2015 | Bardy | A61B 5/04087 600/301 |
| 2016/0015289 A1* | 1/2016 | Simon | A61B 5/04842 600/301 |
| 2016/0095527 A1* | 4/2016 | Thng | A61B 5/6808 600/301 |
| 2016/0242654 A1* | 8/2016 | Quinlan | A61B 5/1123 |
| 2017/0251967 A1* | 9/2017 | Premsukh | A61B 5/0004 |
| 2017/0281074 A1* | 10/2017 | D'Lima | A61B 5/0488 |
| 2019/0015008 A1* | 1/2019 | Alizadeh | A61B 5/6832 |

OTHER PUBLICATIONS

Archive of 'firstbeat.com' [online]. "Smart Wellness Coaching," archived on Dec. 21, 2016 via Internet Archive: Wayback Machine URL<https://web.archive.org/web/20161221190331/https://www.firstbeat.com/en/>. 5 pages.
"Qardio," Retrieved from the internet on Jul. 3, 2018, Retrieved from the Internet: URL<https://www.getqardio.com>. 1 page.
Archive of 'getqardio.com' [online]. "Qardio," archived on Sep. 20, 2016, via Internet Archive: Wayback Machine URL<https://web.archive.org/web/20160920120859/https://www.getqardio.com/>. 1 page.
"AmpStrip—Comfortable 24-7 heart rate wearable," Retrieved from the internet on Jul. 3, 2018, Retrieved from the Internet: URL<https://www.indiegogo.com/projects/ampstrip-comfortable-24-7-heart-rate-wearable#/>. 16 pages.
"FitPal—The Most Complete 24/7 Heart Rate Wearable," Retrieved from the internet on Jul. 3, 2018, Retrieved from the Internet: URL<https://www.kickstarter.com/projects/coreywilliams/fitpal-the-most-complete-24-7-heart-rate-wearable/comments?cursor=12298854>. 19 pages.
"Reshaping Healthcare Improving human health through wearable healthcare solutions," Retrieved on Jul. 3, 2018, Retrieved from the Internet: URL<https://www.mc10inc.com>. 9 pages.
Archive of 'mc10inc.com' [online]. "Reshaping Healthcare Improving human health through wearable healthcare solutions," archived on Oct. 8, 2016, via Internet Archive: Wayback Machine URL <https://web.archive.org/web/20161008084812/http://mc10inc.com/>. 6 pages.
"Polar," Retrieved from the Internet on Jul. 3, 2018, Retrieved from the Internet: URL<https://www.polar.com/us-en>. 10 pages.
Archive of 'polar.com' [online]. "Polar," archived on Sep. 30, 2016, via Internet Archive: Wayback Machine URL <https://web.archive.org/web/20160930095047/https://www.polar.com/us-en>. 5 pages.
"Startup Diaries: Vytal—Week 1," Oct. 4, 2017, Retrieved on Jul. 3, 2018 from the Internet: URL<https://thechungreport.com/startup-diaries-vytal-week-1/>. 10 pages.
"Wichita State startups receive award money at entrepreneurship competition," Apr. 24, 2017, Retrieved on Jul. 3, 2018 from the Internet: URL<https://thesunflower.com/17455/news/wsu-startups-receive-award-money-at-entrepreneurship-competition/>. 5 pages.
"Fully disposable. Functionally indispensable." Retrieved on Jul. 3, 2018, Retrieved from the Internet: URL<https://vitalconnect.com/solutions/vitalpatch/>. 2 pages.
"Kansas startups win $60K from WSU Jumpstart competition," Feb. 17, 2017, Retrieved on Jul. 3, 2018 from the Internet: URL<http://www.wsuventures.org/about-us/in-the-news/kansas-startups-win-60000-from-wsu-jumpstart-competition>. 3 pages.

\* cited by examiner

BODY-WORN BIOMETRIC SENSOR

TECHNICAL FIELD

This document describes systems and methods for detecting and monitoring physiological parameters, for example, to provide personal or team fitness tracking during exercise or other physical activity.

BACKGROUND

When a person engages in physical activity, certain bodily process change, including pulse, breathing rate, blood pressure, and body temperature. In some circumstances, a user can carry a personal fitness tracking device, such as a pedometer, to track the user's activity levels over particular periods of time or throughout his or her normal daily activities. Such pedometer devices may be used to provide an estimate of the user's "steps" accumulated over time, the number of "staircases" climbed, and the number of calories used (which is usually calculated via an extrapolation calculation based upon the user's weight). In some cases, these estimated results can be displayed directly on the personal fitness tracking device or via a personal computing device. Such personal fitness tracking devices are commonly provided in a portable housing (including costly electronics and rechargeable batteries) that is mechanically clips to an article of clothing or carried in a pocket, which often leads to such devices being both costly and requiring reusability over many months or years.

SUMMARY

Some embodiments described herein provide a system and method for tracking and viewing a user's physiological parameters (such as a selected set of exercise parameters indicative of bodily functions during a workout or practice) before, during, and after physical activity. In some versions, a sensor device can be worn on a user's body and is configured to detect multiple physiological parameters and to wirelessly communicate with a mobile computing device, such as a smartphone, tablet, or portable computer. Optionally, the detected physiological parameters can be used to determine a selected set of work-out parameters, such as power, performance, strain, and recovery level, which can be concurrently displayed on the mobile computing device during the user's exercise/activity or after the exercise period for purposes of coaching, comparison to previous exercise periods, or comparison to other users performing the same exercise/activity. In some implementations, each of a plurality of users (e.g., each player on a team) can wear a respective body-worn sensor device, and all of the sensors devices can wireless communicate with a designated mobile computing device, such as a tablet device of a coach, trainer, or judge, for purposes of collectively (and concurrently) monitoring sets of physiological parameters for all of the users during the same workout, practice, or other activity.

In some embodiments, the sensor device may include a multi-piece design (e.g., a two-piece design in some examples described below) in which the pieces are configured to mechanically and releasably couple together prior to the user's physical activity and to detach from one another after the user's physical activity. Optionally, the body-worn sensor can have a two-piece configuration in which a first piece mechanically and releasably attaches to a second piece, which is configured to adhere or otherwise attach to the user during the user's physical activity. For example, the first piece can have a housing that contains a power source, processor, memory, a pulse oximeter, an accelerometer, a temperature sensor, electrocardiogram (ECG) detection circuitry, and at least one ECG lead. Also, in this example, the second piece can include a flexible body configured to adhere to the user's skin, at least a second ECG lead, and a connection device for mechanically and releasably mating with the first piece and for providing an electrical connection from the second ECG lead to the first piece. Optionally, the second piece may have a structure that is disposable and non-reusable (e.g., a "single-use" component), while in other embodiments, the second piece may comprise a portion of a user's garment or other reusable body-worn article. Also, the first piece may optionally have a smaller size than the second piece and may be configured to be reused with a series of subsequent second pieces, for example, over a period of days. The body-worn sensor may include mechanical coupling for securing the first piece to the second piece, for example mating threads. The body-worn sensor may include physical structure for attaching to a user's body, for example adhesive.

In particular embodiments, the body-worn sensor may wirelessly communicate with a computing device, for example a smartphone, tablet, portable computer, or other computing device. The body-worn sensor may communicate with the user's computing device, a monitor's computing device (e.g., computing device of a coach, trainer, judge, or other monitor), or one or more computing devices connected to a computer network. The body-worn sensor may wirelessly communicate physiological parameters, for example blood pressure, pulse, body temperature, and repetitions of a particular physical activity. The computing device may display both physiological parameters and work-out parameters (e.g., parameters such as power, performance, strain, and recovery level), which may be determined based upon the physiological parameters and other factors. Work-out parameters may be determined in the body-worn sensor, in the computing device, or in a different device connected to a computing device via a network. Physiological parameters and work-out parameters may be stored on the network and accessible by the user or a monitor.

In further embodiments, a plurality of body-worn sensors can wirelessly and contemporaneously communicate with a designated computing device, such as the computing device of a coach, trainer, judge, or other monitor. The monitor's computing device may contemporaneously display physiological or work-out parameters corresponding to the plurality of sensors, which may be worn by a plurality of users competing or participating in a workout, sport, practice, exercise, or other physical activity. Optionally, the monitor may also be a user that wears one of the body-worn sensors.

Some or all of the embodiments described herein may provide one or more of the following advantages. First, some embodiments allow the user to engage in physical activity while wearing a body-worn sensor in a substantially unencumbered manner. This ensures that the user's physical activity would be nearly the same if performed without wearing the sensor.

Second, in some embodiments, a user engaged in physical activity can view physiological parameters and work-out parameters in real time on a computing device. Such a configuration may beneficially assist the user in deciding whether and how to alter his or her physical activity for purposes of an enhanced/personalized training or purposes of safety.

Third, in some embodiments, a user can track multiple physical-activity sessions over time and compare the same set of physiological parameters and/or work-out parameters among the various physical-activity sessions. This allows a user to vary the number, scope, and intensity of physical-activity sessions as desired.

Fourth, in some embodiments a user can upload parameters (e.g., the user's physiological parameters and work-out parameters for a selected workout or other physical activity) via a network, enabling a monitor to remotely access and view the user's parameters and enabling the user to archive a larger set of physical-activity sessions in a remote computing device. Such a configuration provides the optional benefit of providing the monitor, who might be more knowledgeable than the user about physical activity even though the monitor is located remotely from the user, with an opportunity to give the user feedback about whether and how to vary the physical-activity sessions.

Fifth, in some embodiments, a monitor can contemporaneously track multiple users that are each wearing respective body-worn sensors in communication with the monitor's computing device. Such a configuration enables the monitor to compare performance among users and provide different feedback to different users in real time during the training session or other physical activity. Optionally, the monitor's computing device can wirelessly communicate directly with the body-worn sensors carried by the multiple users, or some or all of the body-worn sensors carried by the multiple users can wirelessly communicate with an intermediate computing device that then communicates with the monitor's computing device (e.g., via a network) so that the monitor can track the multiple users during a training session even though some users are located remotely from the monitor.

The details of one or more embodiments of the invention are set forth in the accompanying drawings and the description herein. Other features, objects, and advantages of the invention will be apparent from the description and drawings, and from the claims.

DETAILED DESCRIPTION OF ILLUSTRATIVE EMBODIMENTS

Figure 1:
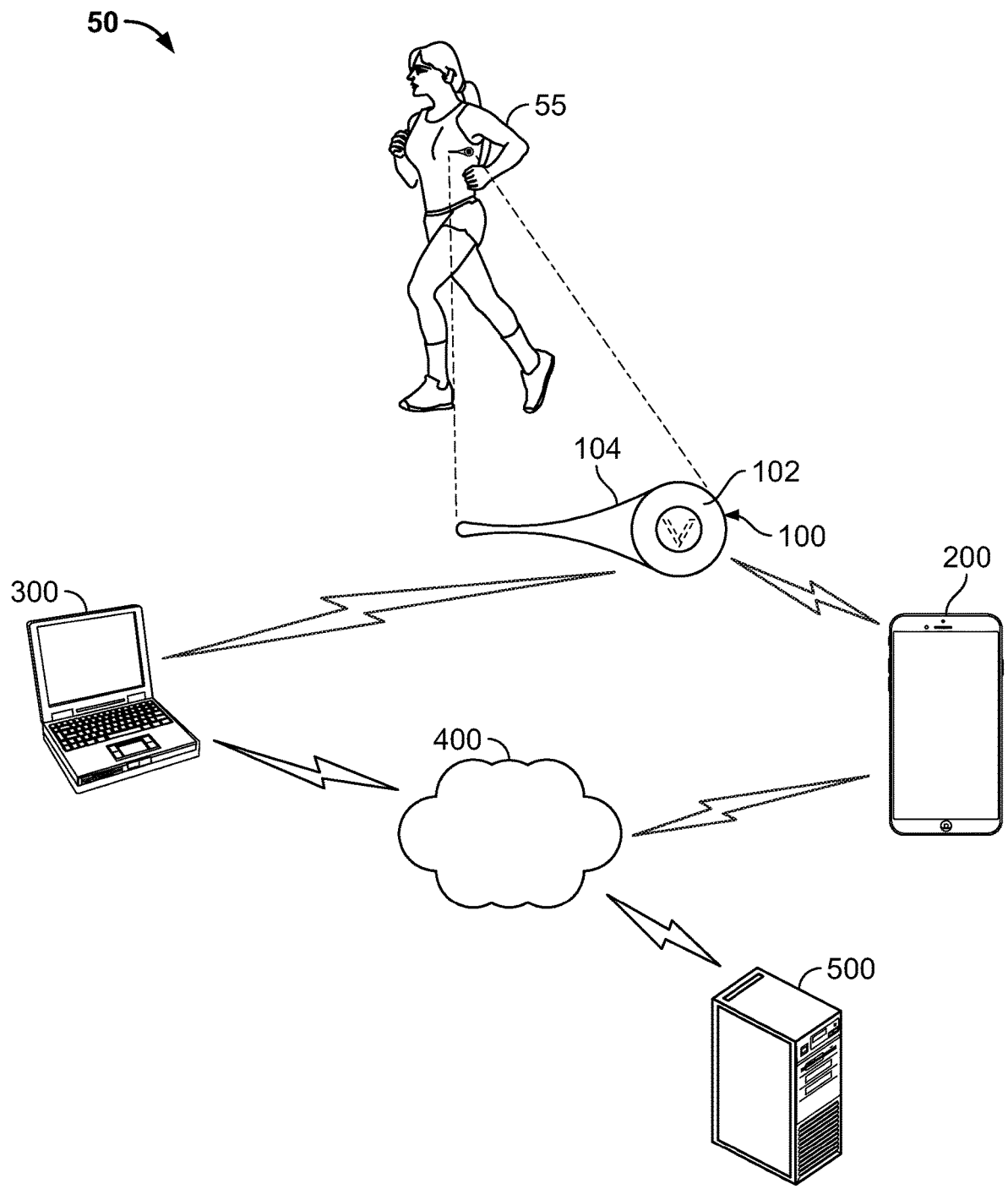
FIG. 1 is a diagram of a physical activity monitoring system, in accordance with some embodiments provided herein.

Referring to FIG. 1, some embodiments of a system 50 include a sensor device 100 worn by a user 55 and configured to wirelessly communicate with one or more computing devices 200 and 300, for example, using a short-range communication protocol. As will be described further below, the sensor device 100, which in this embodiment is a body-worn sensor, is equipped with one or more sensor instruments configured to measure one or more physiological parameters of the user 55, and can wirelessly communicate information relating to the measured parameters to the other external devices 200 and 300. The computing devices in communication with the body-worn sensor 100 are dependent on the configuration of the system 50. For example, in some embodiments the system 50 can optionally include one or more of a user's computing device 200, a monitor's computing device 300, a remote server 500 connected to device 200 or 300 via a network 400 (such as the Internet), and other computing devices equipped to receive and store information generated from the sensor device 100. However, such external devices are optional, and some embodiments of the system 50 may have none of, or only a subset of, these aforementioned external devices and networks 200, 300, 400, and 500.

In particular embodiments, the sensor device 100 wirelessly communicates with at least one computing device 200/300, such as a smartphone, tablet, portable computer, or other computing device. Preferably, each of the computing devices 200/300 is equipped with a wireless communication device (e.g., a short-range communication protocol such as Bluetooth or near-field communication (NFC), a wifi communication device for RF communication with a local wireless network, or the like). As described in more detail below, the sensor device 100 may communicate with the user's computing device 200, the monitor's computing device 300 (e.g., computing device of a coach, trainer, judge, or other monitor), or a one or more computing devices 500 connected to a network 400 for purposes of providing real-time information of the user's physiological parameters during a physical-activity session. For example, the sensor device 100 may be in the form of a body-worn sensor that wirelessly communicates physiological parameters selected from the group consisting of blood pressure, pulse rate, body temperature, and repetitions of a particular physical activity (e.g., steps, lifts, cycles, or the like). The computing device 200, 300, or 500 may display both physiological parameters and work-out parameters, which can be calculated based at least partially upon the physiological parameters detected by the sensor device 100. The work-out parameters may include parameters such as power, performance, strain, and recovery level, any or all of which are preferably determined at the computing device 200, 300, or 500 (or may alternatively be determined at the sensor device 100 and communicated therefrom). Additionally, the physiological parameters and work-out parameters may be stored at the computing device 200, 300, or 500 for subsequent access by the user or a monitor.

Briefly, in use, the system 50 can provide for tracking and viewing a selected set of exercise parameters indicative of the user's bodily functions during a workout, training session, athletic practice, or other physical activity, which can be monitored and viewed in real time during the user's physical activity and also accessed after the physical activity. For example, the sensor device 100 can be adhered to an athlete's skin during a training session so that a set of sensor instruments (e.g., a pulse oximeter, an accelerometer, a temperature sensor, and an ECG sensing circuit) are mounted to the athlete and arranged to detect a set of parameters. As described in in connection with FIGS. 7A-D, the detected physiological parameters can be used to determine a selected set of work-out parameters (e.g., power, performance, strain, and recovery level), and some or all of the physiological parameters and work-out parameters can be concurrently displayed on the mobile computing device 200, 300 during the user's exercise/activity or after the exercise period for purposes of coaching, comparison to previous exercise periods, or comparison to other users performing the same exercise/activity. As described in in connection with FIGS. 8-9, a plurality of users 55 (e.g., each player on a team, competitors in a competition, or another set of users) can wear a respective sensor device 100, and all of the sensor devices 100 can wirelessly communicate with a designated mobile computing device 300, such as a tablet device of a coach, trainer, or judge, for purposes of collectively (and concurrently) monitoring sets of physiological parameters for all of the users during the same workout, practice, competition, or other activity.

Figure 2:
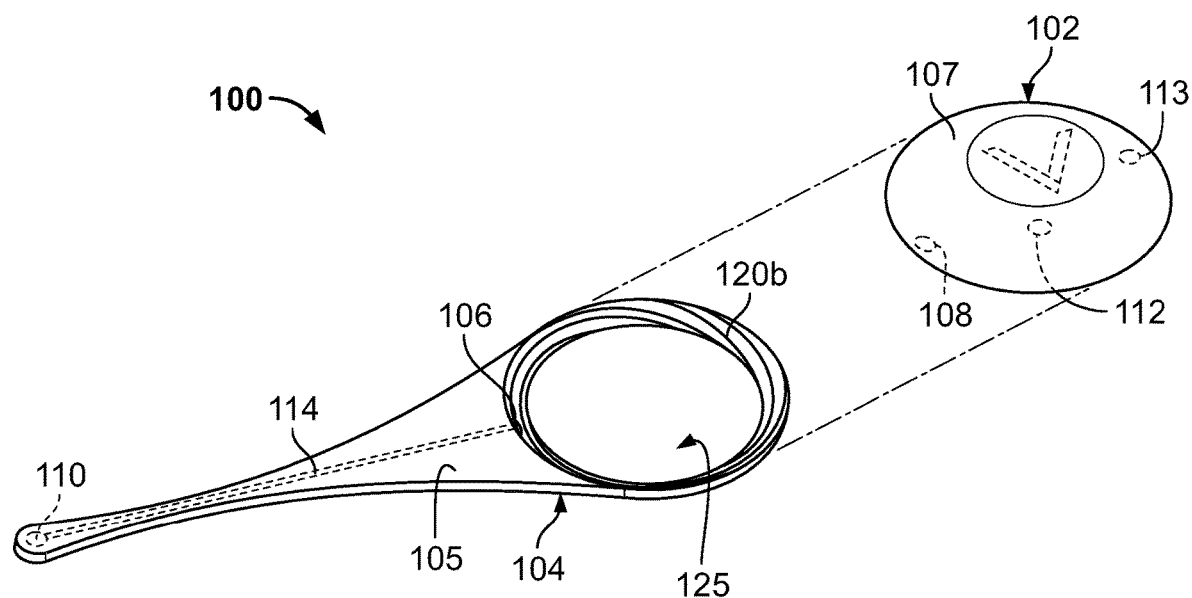
FIG. 2 is a perspective exploded view of a sensor device of the physical activity monitoring system of FIG. 1, in accordance with some embodiments.
Figure 3:
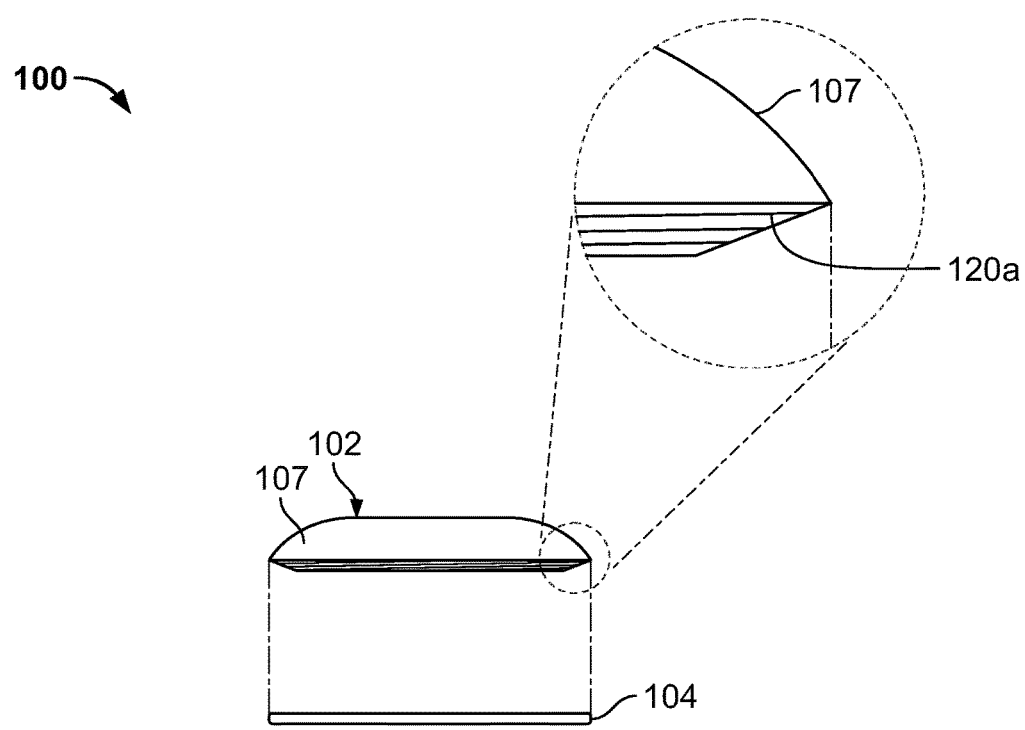
FIG. 3 is a side view of the sensor device of FIG. 2.
Figure 4:
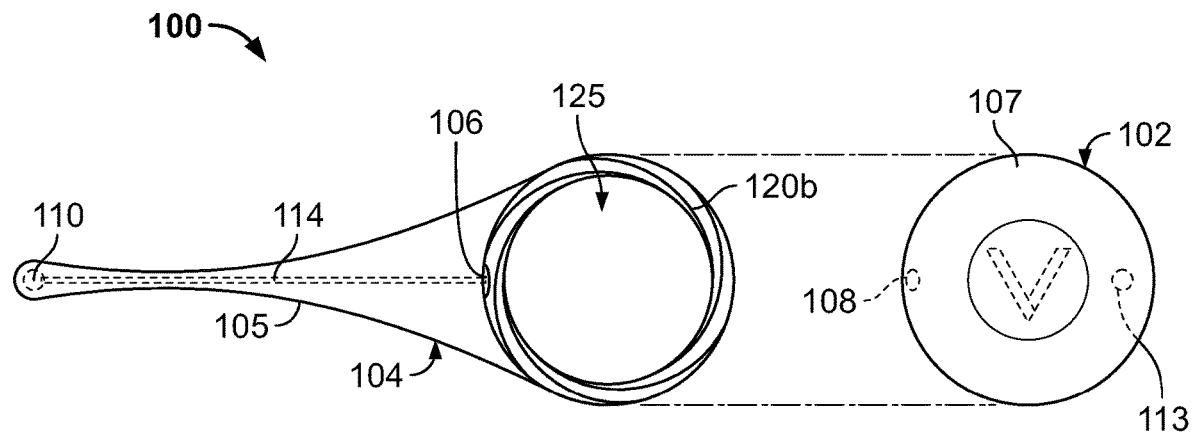
FIG. 4 is a top view of the sensor device of FIG. 2.
Figure 5:
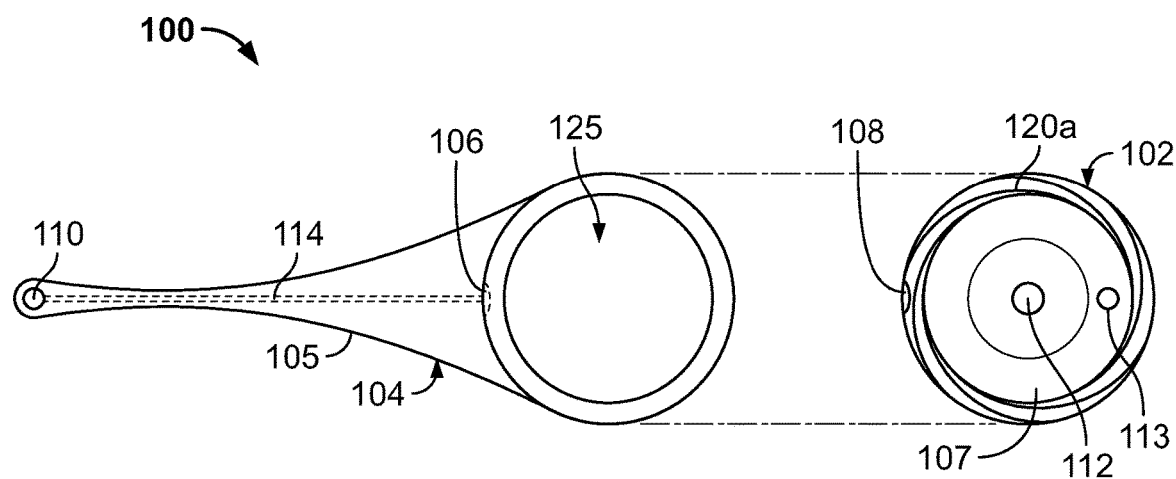
FIG. 5 is a bottom view of the sensor device of FIG. 2

Referring now to FIGS. 1-2, some embodiments of the sensor device 100 may include a multi-piece configuration in which a user can mechanically and releasably couple the pieces together prior to the user's physical activity and can detach the pieces from one another after the user's physical activity. For example, in this embodiment, the sensor device 100 comprises a first piece 102 and a second piece 104. As shown in FIG. 2, the first piece 102 of the sensor device 100 mechanically and releasably attaches to the second piece 104, and the second piece 104 has a flexible body 105 with an adhesive layer along its lower surface to adhere the user's skin during the user's physical activity. As described in more detail below, the first piece 102 has an external housing 107 that contains (preferably in a sealed, water-tight arrangement) at least a power source, processor, memory, a pulse oximeter, an accelerometer, a temperature sensor, and electrocardiogram (ECG) detection circuitry. The first piece 102 can further include at least a first ECG lead 112 (refer also to FIG. 5) connected to the ECG detection circuitry and exposed along the external housing 107 at a position to engage with the user's skin surface during use. Also, in this embodiment, the flexible body 105 of the second piece 104 has at least a second ECG lead 110 embedded therein with a contact region arranged at a position along the underside of the flexible body 105 to engage with the user's skin surface during use. As described in more detail below, the first and second pieces 102 and 104 have mating electrical connectors 106 and 108 to provide an electrical connection from the second ECG lead 110 to the the ECG detection circuitry within the first piece 102. The sensor device 100 may include mechanical releasably coupling 120, such as mating threads 120a-b, so that the first piece 102 is capable of being physically mounted with and directly connected to the second piece 104 in a removable manner. In some embodiments, the first portion 102 may be reusable, and the second portion 104 may be disposable.

In this embodiment, the second piece 104 has a structure that is disposable and non-reusable (referred to as a "single-use" component). For example, the second piece 104 may have one or more structural features that hinder reuse of the second piece 104 after being worn by the user for a first period, such as the adhesive layer on the underside of the flexible body 105 being configured to maintain its bond with the user's skin only during the first period of time, but not a subsequent period of time after removal from the user's skin. Optionally, the flexible body 105 of the second piece 104 may have an outer periphery that provides a substantially "tear-drop" shape, which enhances a number of features of the sensor device 100 (e.g., providing a lengthwise extension to space the second ECG lead 110 further away from the first ECG lead 112 (on the first piece 102), providing an increased surface area along the underside of the flexible body for improved adhesion to the user's skin, and providing a streamlined shape so that the second piece 104 can be conveniently adhered in a variety of different locations on the user's body). In other embodiments, the second piece 104 may be a garment, or be part of a garment, such as a shirt. As shown in FIG. 2, the first piece 102 in this embodiment has a smaller size than the second piece 104 such that the first piece 102 is configured to nest within an aperture 125 of the second piece 104. As described in more detail below, the first piece 102 may be configured to be reused with a series of subsequent second pieces 104, for example, over a period of days, such as 3 days to 10 days, and preferably a period of 7 days to 10 days, at which time the battery life of the first piece 102 is expired. In alternative embodiments, the first piece 102 may be equipped with a rechargeable power source so that it can be reused over a greater period of time (e.g., greater than 10 days).

Referring now to FIGS. 2-5, sensor device 100 may include mechanical releasably coupling 120, such as mating threads 120a-b, so that the first piece 102 is capable of being physically mounted with and directly connected to the second piece 104 in a removable manner. In some embodiments, a first electrical connector 108 is positioned on the first piece 102 so that the first electrical connector 108 aligns with a second electrical connector 106 on the second piece 104 when the first piece 102 is coupled to the second piece 104. In some embodiments, the first piece 102 is configured to nest within an aperture 125 in the second piece 104. The aperture 125 can be equipped with a female thread, which is configured to mate with a corresponding male thread on the exterior of the first piece 102 (e.g., along a lower inwardly tapered periphery of the second piece 104). The mating threaded engagement (or other attachment mechanism) can be configured with a predefined stop/lock location so that, when the first piece 102 is mechanically secured to the second piece 104, the first electrical connector 108 aligns with the second electrical connector 106 to provide a hard-wired electrical connection between the second ECG lead 110 (proximate to the opposite end of the second piece 104) and the ECG detection circuitry 160 within the first piece 102). The first piece 102 may also include a first ECG lead 112, preferably on a surface of the first piece 102 so that the first ECG lead 112 contacts the skin of a user 55. In such embodiments, the second ECG lead 110 and the first ECG lead 112 may be spaced apart from one another (yet both in contact with the user's skin and interconnected together via other components) by a separation distance of about 1 to 8 inches, and preferably about 3-5 inches in the depicted embodiment. The first piece 102 may also include a pulse oximeter sensor 113, preferably with at least a portion on a surface of first piece 102 so that the pulse oximeter sensor 113 contacts the skin of a user 55. Other sensors may optionally be included.

Sensor device 100 may be 1 to 8 inches long (a maximum extending from the tip of the second piece 104 to the opposite end), and is preferably 3-5 inches long in the embodiment depicted in FIGS. 2-5. The first piece 102 may have a maximum dimension (e.g., the diameter in this embodiment) that is one-half inch to two inches, and preferably about one inch in the embodiment depicted in FIGS.

2-5. The first piece 102 may weigh up to 3 or 4 ounces, is preferably less than two ounces, and weighs 0.25-1 ounces in the embodiment depicted in FIGS. 2-5. In the preferred embodiment, the length of the second piece 104 is configured such that a second ECG lead 110 on the second piece 104 may be at a predefined distance from a first ECG lead 112 on the first piece 102 such that ECG detection circuitry 160 operates effectively. The second piece 104 may weigh up to 2 or 3 ounces, and preferably less than one ounce in the embodiment depicted in FIGS. 2-5. The second piece 104 may include a flexible body 105, which in this embodiment, comprises a flexible web of polymer material with a biocompatible adhesive layer for attachment to the skin of user 55.

Figure 6A:
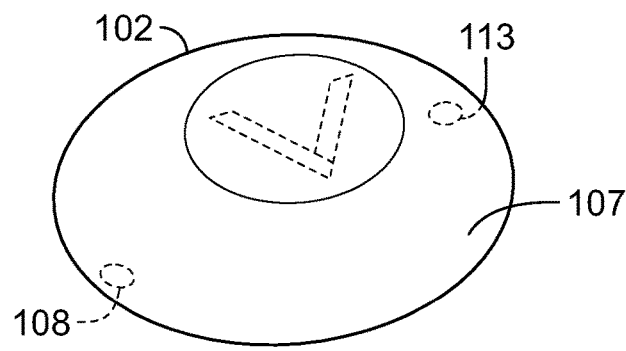
FIG. 6A is a perspective view of a first piece of the sensor device of the physical activity monitoring system of FIG. 1, in accordance with some embodiments.
Figure 6B:
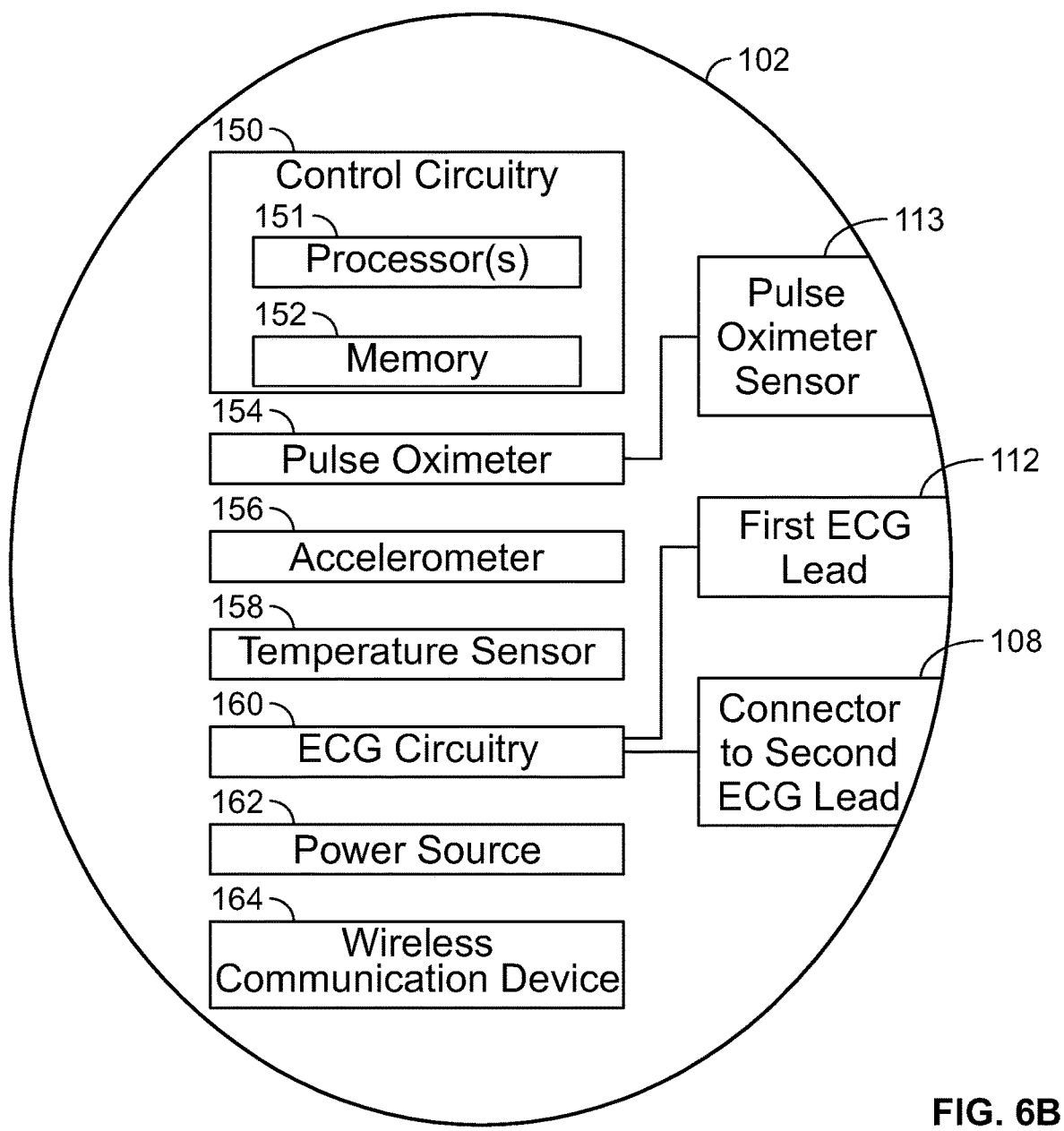
FIG. 6B is a diagram of internal circuitry and sensor elements housed within the first piece of the sensor device of the physical activity monitoring system of FIG. 1, in accordance with some embodiments.

Referring now to FIGS. 6A-B, the first piece 102 of the sensor device 100 can have a relatively small disc-shaped form. Preferably, the first piece 102 has a size that is small enough to reduce the likelihood of encumbering the user 55 during his or her physical activity. Additionally, the first piece 102 has a size sufficient to house control circuitry 150, multiple physiological sensor instruments 154, 156, 158, 160, a power source 162, and a wireless communication device 164.

Control circuitry 150 may include at least one processor 151 and memory 152. Control circuitry 150 may be configured to receive data, physiological parameters, and/or work-out parameters from one or more physiological sensor instruments 154, 156, 158, 160; store data, physiological parameters, and/or work-out parameters in memory 152; and convert data or physiological parameters from one or more physiological sensor instruments 154, 156, 158, 160 into other physiological parameters or work-out parameters.

Sensor device 100 may include at least one accelerometer 156. Accelerometer 156 may optionally detect a user's physical movements, such as whether the user has started or stopped running. Thus, a benefit of some embodiments is to detect and measure the user's physical movements.

Sensor device 100 may include a pulse oximeter 154 including a pulse oximeter sensor 113. Pulse oximeter sensor 113 may be structurally separate but in electrical continuity with pulse oximeter 154, or pulse oximeter sensor 113 may be integrated with pulse oximeter sensor 154. Pulse oximeter 154 may measure both the user's heartrate or pulse, and the user's oxygen saturation. Preferably, pulse oximeter 154 utilizes an infrared light-emitting diode and measures the amount of infrared light that the user's blood absorbs. Some components or functions of pulse oximeter 154 may be located or performed in control circuitry 150 (for example, in some embodiments, the absorption data can be converted into an oxygen saturation value using the control circuitry).

During physical activity, a user's heartrate or pulse typically increases relative to the intensity of the physical activity. For example, a user's resting heartrate may be as low as 40-50 beats per minute, but as high as 180-200 beats per minute during intense physical activity. During physical activity, a user's oxygen saturation may fluctuate or decrease slightly. For example, a user's resting oxygen saturation may be approximately 98%, but may fluctuate or drop a few percent during physical activity. If oxygen saturation drops below 90%, the user may experience hypoxia. Thus, a benefit of some embodiments may be to detect a potentially dangerous drop in a user's oxygen saturation.

In some embodiments, sensor device 100 includes a temperature sensor 158 that can measure a user's body temperature, either directly or indirectly. For example, in the preferred embodiment, temperature sensor 158 includes a thermocouple, which may detect a voltage change induced by the thermoelectric effect. In other embodiments, temperature sensor 158 may include a resistance thermometer, an infrared thermometer, or a bimetallic thermometer. Temperature sensor 158 may include a temperature sensor lead capable of contacting the user's skin for, among other things, improved accuracy of temperature readings.

During and after physical activity, a user's body temperature may change. Physical activity causes a person's muscles to generate more heat than when the person is at rest. Natural bodily processes such as increased perspiration often help dissipate the extra heat generated by the muscles. Environmental conditions such as ambient temperature and humidity may affect these natural bodily processes. For example, a user that is conducting physical activity in a hot and humid environment may experience a rise in body temperature, which could lead to overheating, heat exhaustion, or dehydration. When a user engaged in physical activity for an extended period of time (e.g. more than 30 minutes), quickly stops (e.g. does not "cool down"), the user's muscles may quickly stop generating more heat, but the natural bodily processes that cool the body may not stop as quickly. This may cause post-exercise hypothermia. Thus, a benefit of some embodiments may be to detect both dangerously high and dangerously low body temperatures during or after physical activity.

In some embodiments, sensor device 100 includes an electrocardiogram (ECG) detection circuitry 160. The sensor device 100 may include a first ECG lead 112, which may be on the first piece 102, and a second ECG lead 110, which may be on the second piece 104, to operate with ECG detection circuitry 160. The second ECG lead 110 may be capable of being electrically connected to the first piece 102 via a connection 114 and connector 106. Generally, ECG detection circuitry 160 operates by detecting at the skin the electrical signals that stimulate the heart. ECG detection circuitry 160 may detect, among other things, the electrical signals of the user's heart, blood pressure, and/or pulse.

During physical activity, a user's pulse typically increases, as previously discussed. During physical activity, a user's blood pressure may increase as well. For example, a user's systolic pressure may increase as the heart works to deliver increased amounts of blood to the muscles. A user that engages in regular physical activity (e.g. at least 3 times per week for at least 30 minutes each session) may strengthen his or her heart and/or cardiovascular system, thereby lowering the user's pulse and blood pressure during successive physical-activity sessions. Thus, a benefit of some embodiments may be to track a user's pulse and blood pressure over successive physical-activity sessions. ECG detection circuitry 160 may also detect electrical signals indicative of a heart abnormality (e.g. arrhythmia). Thus, a benefit of some embodiments may be to detect heart and/or cardiovascular abnormalities.

Sensor device 100 may include a power source 162, which may preferably be a non-rechargeable battery. For example, power source 162 may be a disc-shaped non-rechargeable battery, with an electrical potential of approximately 2-5 volts, and a size of approximately one-quarter inch to one and one-half inches in diameter. Power source 162 may also be a rechargeable power source, such as a rechargeable battery, capable of being removed from sensor device 100 for recharging. Power source 162 may also be rechargeable power source capable of being recharged without removing power source 162 from sensor device 100 or the first piece 102.

In some embodiments, sensor device 100 may include a wireless communication device 164, which may preferably include a Bluetooth communication device with an antenna and communication circuitry. Wireless communication device 164 may optionally include a near-field communication (NFC) device and/or a wifi communication device. Wireless communication device 164 may be capable of sending and receiving data, physiological parameters and/or work-out parameters between sensor device 100 and computing devices 200, 300. For example, a user 55 may conduct physical activity with computing device 200 within the range of wireless communication device 164 (e.g., going for a run while carrying a smartphone in an armband). Transmission of data, physiological parameters and/or work-out parameters may occur contemporaneously with the user's physical activity, or after the user has completed his or her physical-activity session.

Figure 7A:
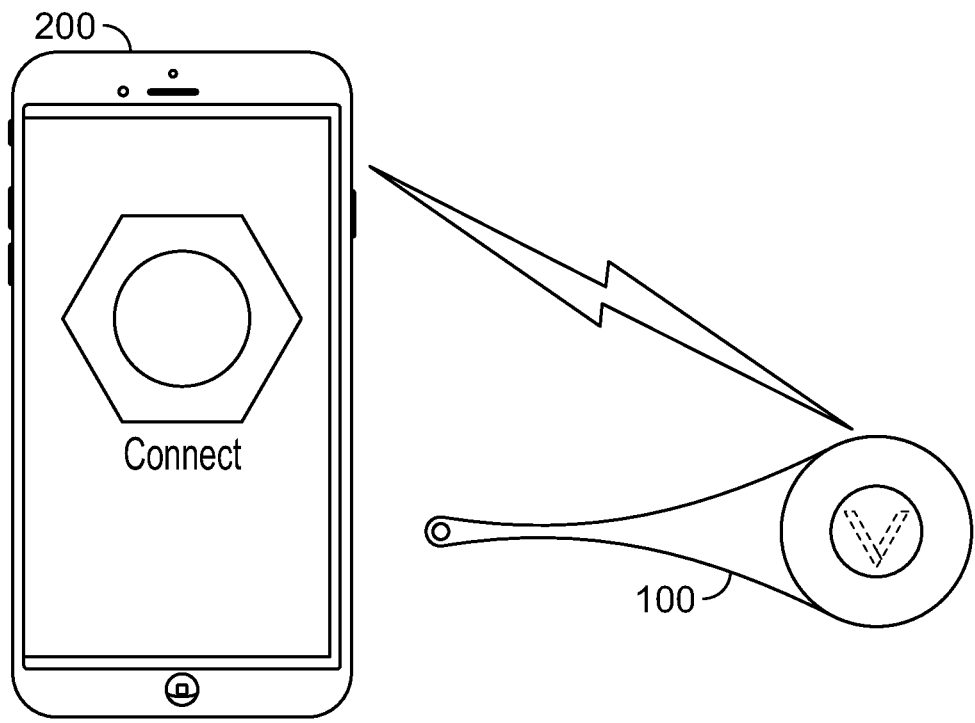
FIGS. 7A-7D illustrate example screen shots of a user's computing device of the physical activity monitoring system of FIG. 1, in accordance with some embodiments.
Figure 7B:
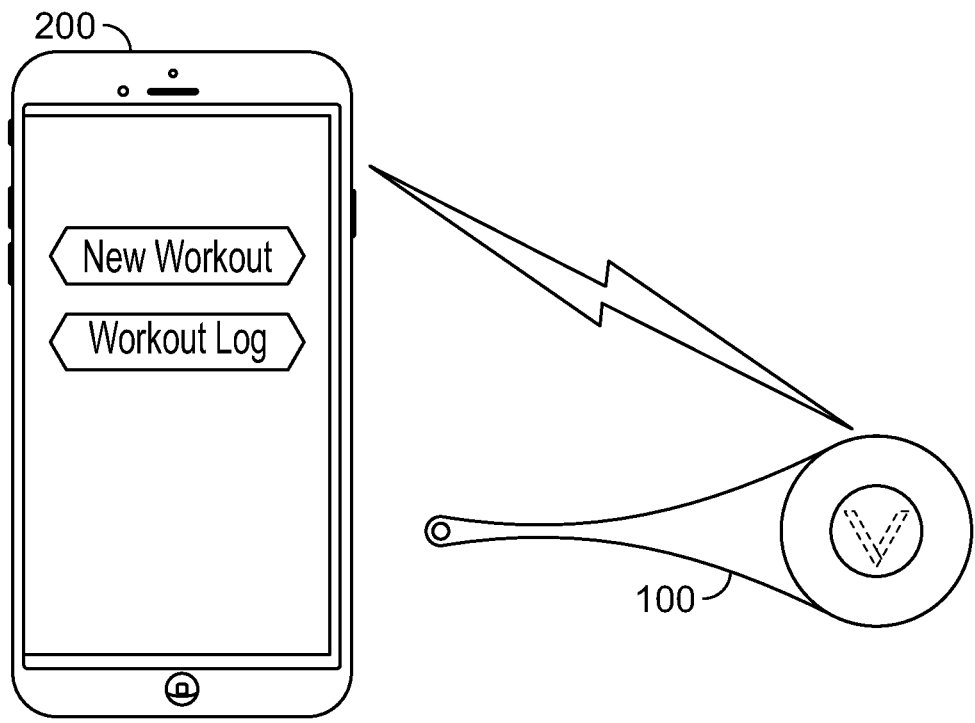
Figure 7C:
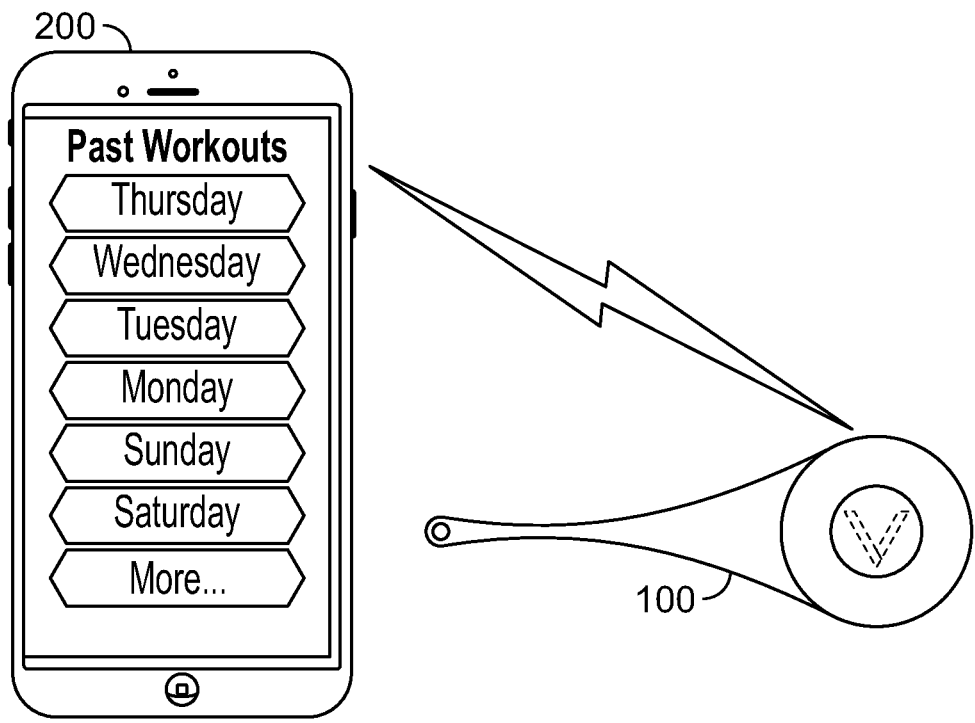
Figure 7D:
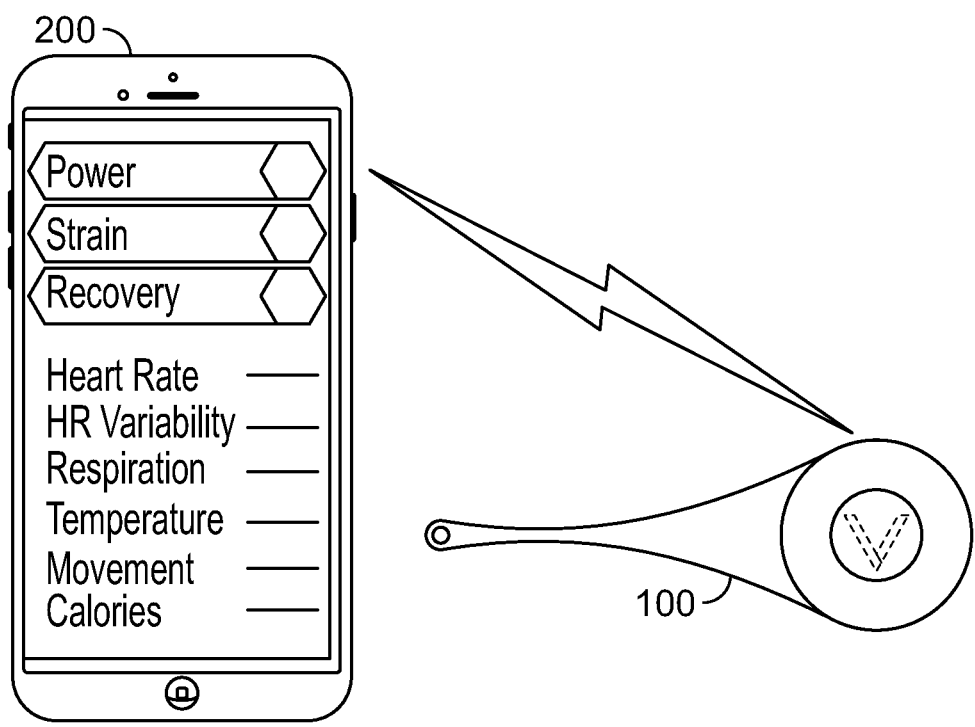

Referring now to FIGS. 7A-D, in some embodiments, sensor device 100 may be configured to wirelessly communicate with computing device 200, 300. Optionally, computing device 200, 300 may be a mobile computing device, such as a smartphone. Computing device 200, 300 may include a user interface (e.g., a display screen) that enables the user to establish a wireless connection between computing device 200, 300 and sensor device 100, for example as shown in FIG. 7A. Computing device 200, 300 may be configured to store data, physiological parameters and/or workout parameters. The user interface of computing device 200, 300 may enable the user to view data, physiological parameters and/or workout parameters from a plurality of physical-activity sessions, such as workouts from previous days of the week, for example as shown in FIGS. 7B-7C. Computing device 200, 300 may include a user interface that displays data, physiological parameters and/or workout parameters. For example, computing device 200, 300 may display power, strain, recovery, heart rate or pulse, or temperature or body temperature, for example as shown in FIG. 7D.

Figure 8:
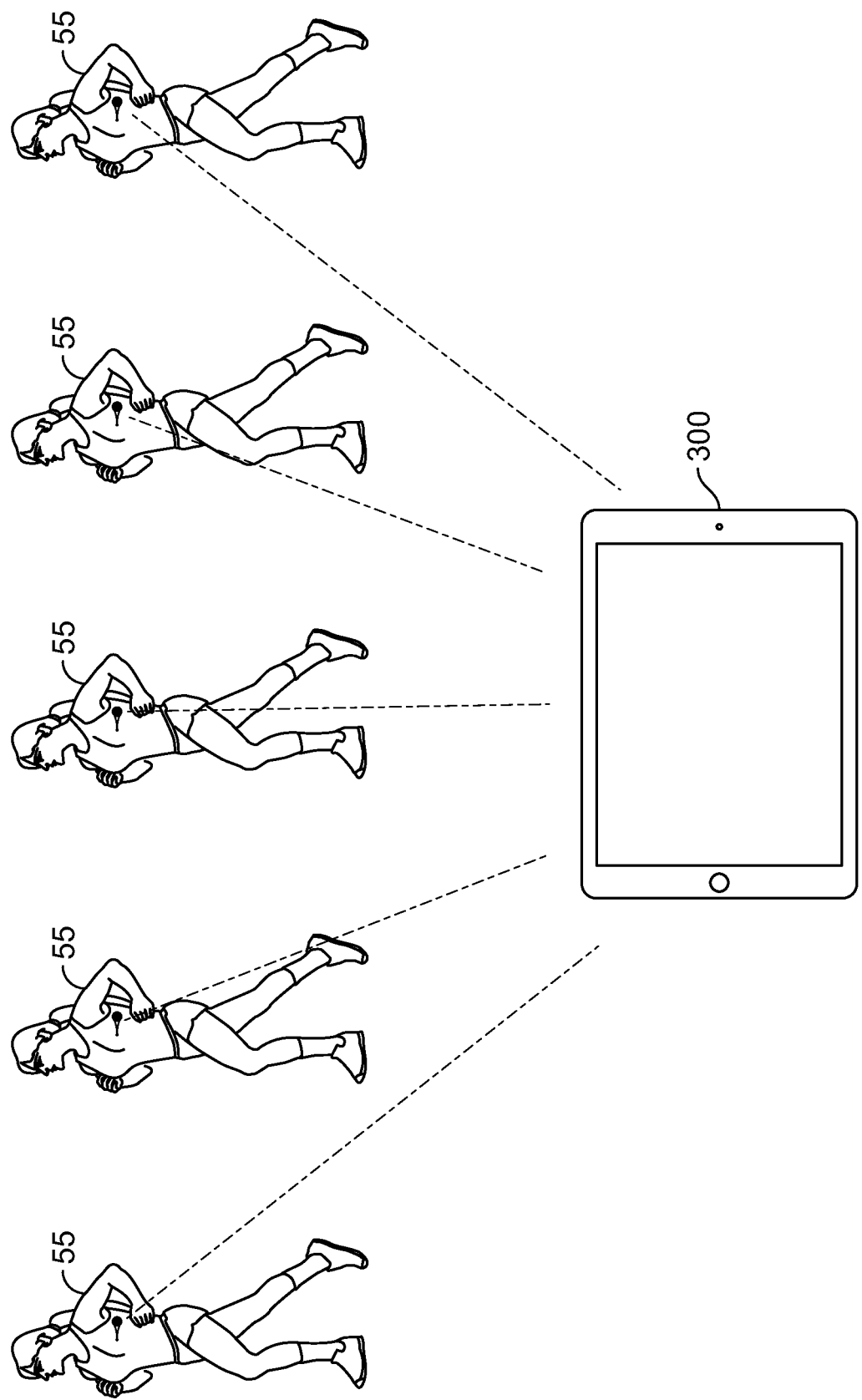
FIG. 8 depicts a plurality of body-worn sensors in communication with a monitor's computing device of the physical activity monitoring system of FIG. 1, in accordance with some embodiments.
Figure 9:
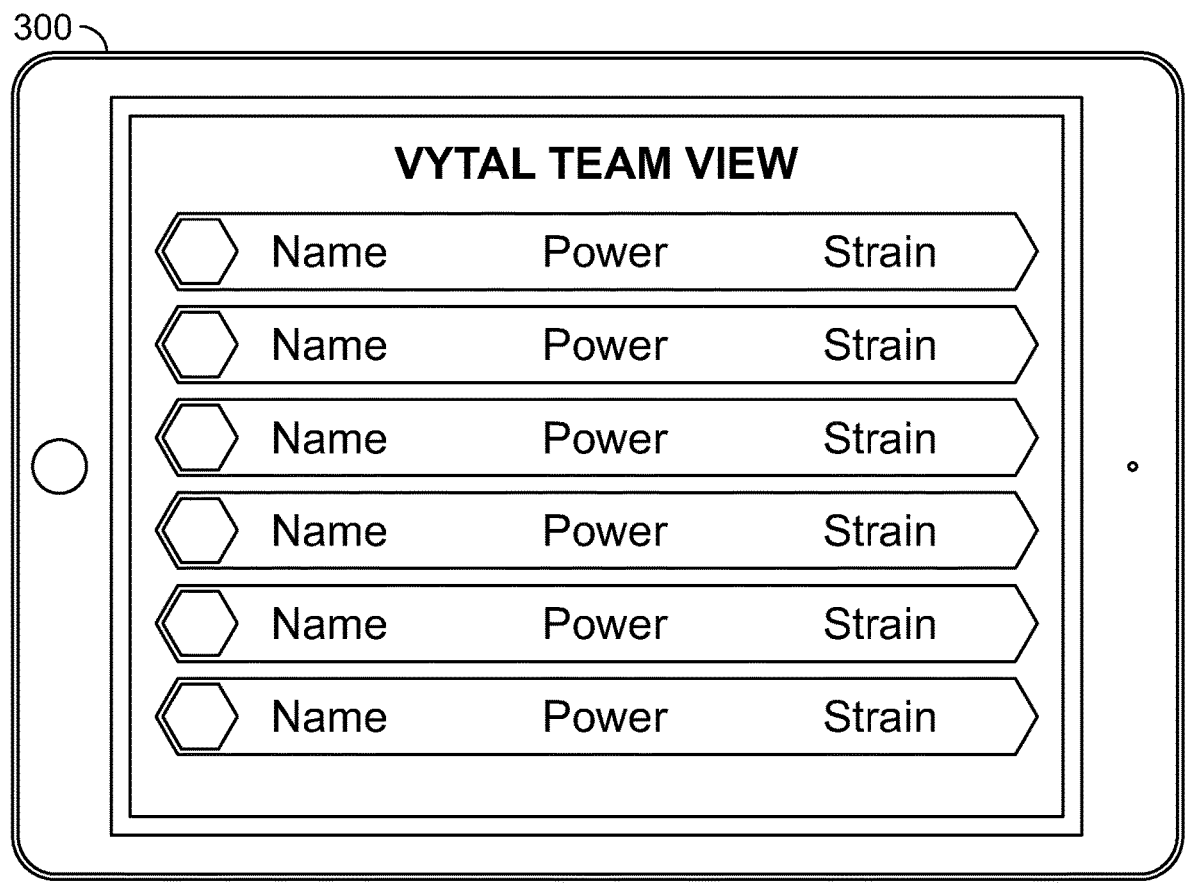
FIG. 9 illustrates an example screen shot of the monitor's computing device of FIG. 9, in accordance with some embodiments.

Referring now to FIGS. 8-9, in other embodiments, a plurality of sensor devices 100 can wirelessly and contemporaneously communicate with a designated computing device 300, such as the computing device of a coach, trainer, judge, or other monitor. Computing device 200, 300 may include a user interface (e.g., a display screen) for a monitor (e.g., a coach or judge), enabling a monitor to view data, physiological parameters and/or workout parameters corresponding to each user 55. The monitor's computing device 300 may contemporaneously display physiological or workout parameters corresponding to the plurality of sensor devices 100, which may be worn by a plurality of users 55 competing or participating in a workout, sport, practice, exercise, or other physical activity. Optionally, the monitor may also be a user 55 that wears one of the body-worn sensors.

What is claimed is:

1. A body-worn sensor comprising:
  a first piece of the body-worn sensor that houses a power source, memory, a processor, a pulse oximeter, a temperature sensor, an accelerometer, ECG detection circuitry, a wireless communication device, and a first ECG lead exposed along an exterior of the first piece; and
  a second piece of the body-worn sensor mechanically and releasably attachable to the first piece and including a flexible body with a second ECG lead embedded in the flexible body for communication with the ECG detection circuitry housed within the first piece, wherein the second ECG lead extends through the flexible body and both the first ECG lead of the first piece and the second ECG lead of the second piece are externally exposed on a same side of the flexible body to engage a user's skin surface when the second piece is mechanically and releasably attached to the first piece,
  wherein the second piece includes a biocompatible adhesive layer along an underside of the flexible body to contact a skin surface such that the second piece is disposable and non-reusable after adhesion to a user's body, and
  wherein the second piece defines an aperture, wherein the first piece comprises an exterior housing configured to nest within the aperture defined by the second piece, the exterior housing of the first piece having an attachment mechanism to mechanically and releasably secure to the second piece, wherein the first piece is reusable with a series of second pieces having a form factor the same as said second piece.

2. The body-worn sensor of claim 1, wherein the attachment mechanism comprises a mating threaded engagement with a predefined lock location so that, when the first piece is mechanically secured to the second piece, a first electrical connector exposed along an exterior of the first piece aligns with a second electrical connector exposed along the aperture defined by the second piece to provide a hardwired electrical connection between the second ECG lead embedded within the flexible body of the second piece and the ECG detection circuitry within the housing of the first piece.

3. The body-worn sensor of claim 2, wherein the flexible body of the second piece has an outer periphery with tear-drop shape.

4. The body-worn sensor of claim 2, wherein the exterior housing of the first piece comprises a male portion of the mating threaded engagement and the aperture of the second piece comprises a female portion of the mating threaded engagement, wherein the female portion of the mating threaded engagement is inwardly tapered in the aperture.

5. The body-worn sensor of claim 1, wherein the second piece comprises a garment.

6. The body-worn sensor of claim 5, wherein the garment is a reusable body-worn article of clothing.

7. The body-worn sensor of claim 1, wherein the power source is a rechargeable battery.

8. The body-worn sensor of claim 1 wherein the processor is configured to determine a physiological parameter.

9. The body-worn sensor of claim 8, wherein the physiological parameter is at least one of a pulse, a blood pressure, a temperature, a number of repetitions, a power, a performance, a strain, or a recovery level.

10. The body-worn sensor of claim 1, wherein the first piece has a weight of less than 2 ounces.

11. The body-worn sensor of claim 10, wherein the first piece has a dimension of 0.5 inches to about 2 inches.

12. The body worn sensor of claim 11, wherein the second piece has a weight of less than 1 ounce.

13. The body-worn sensor of claim 1, wherein the flexible body of the second piece comprises a flexible web of polymer.

14. The body-worn sensor of claim 1, wherein the wireless communication device comprises an antenna.

15. The body-worn sensor of claim 14, wherein the wireless communication device is configured to wirelessly communicate with a computing device.

16. The body-worn sensor of claim 15, wherein the computing device is at least one of a user device, a monitor device, or a remote server.

17. The body-worn sensor of claim 15, wherein the wireless communication device is configured to communicate over a short-range communication protocol.

18. A body-worn sensor comprising:
- a first piece that houses a power source, memory, a processor, a pulse oximeter, a temperature sensor, an accelerometer, ECG detection circuitry, a wireless communication device, and a first ECG lead; and
- a second piece mechanically and releasably attachable to the first piece and including a flexible body with a second ECG lead embedded therein for communication with the ECG detection circuitry housed within the first piece,
- wherein the second piece includes a biocompatible adhesive layer along an underside of the flexible body to contact a skin surface such that the second piece is disposable and non-reusable after adhesion to a user's body,
- wherein the first piece comprises an exterior housing configured to nest within a corresponding aperture defined by the second piece, the exterior housing of the first piece having an attachment mechanism to mechanically and releasably secure to the second piece, wherein the first piece is reusable with a series of second pieces having a form factor the same as said second piece,
- wherein the attachment mechanism comprises a mating threaded engagement with a predefined lock location so that, when the first piece is mechanically secured to the second piece, a first electrical connector exposed along an exterior of the first piece aligns with a second electrical connector exposed along the corresponding aperture defined by the second piece to provide a hardwired electrical connection between the second ECG lead embedded within the flexible body of the second piece and the ECG detection circuitry within the housing of the first piece, and
- wherein the first ECG lead of the first piece extends to a first lead end at an exterior lower surface of the housing of the first piece so that the first ECG lead contacts the skin surface when the flexible body of the second piece is adhered to the skin surface, and wherein the second ECG lead extends through the flexible body of the second piece to a second lead end at an exterior lower surface of the flexible body of the second piece such that the second lead end of the second ECG lead and the first lead end of the first ECG lead are spaced apart from one another by a separation distance of 2.5-5 inches.

19. The body-worn sensor of claim 18, wherein the flexible body of the second piece has an outer periphery with tear-drop shape.

20. The body-worn sensor of claim 18, wherein the second piece comprises a garment.

21. The body-worn sensor of claim 18, wherein the processor is configured to determine a physiological parameter, wherein the physiological parameter is at least one of a pulse, a blood pressure, a temperature, a number of repetitions, a power, a performance, a strain, or a recovery level.

22. The body-worn sensor of claim 18, wherein the flexible body of the second piece comprises a flexible web of polymer.

23. The body-worn sensor of claim 18, wherein the exterior housing of the first piece comprises a male portion of the mating threaded engagement and the aperture of the second piece comprises a female portion of the mating threaded engagement, wherein the female portion of the mating threaded engagement is inwardly tapered in the aperture.

* * * * *